United States Patent
Wang et al.

(10) Patent No.: US 9,155,516 B2
(45) Date of Patent: Oct. 13, 2015

(54) APPARATUS AND METHOD FOR COUNT LOSS CALIBRATION OF PHOTON-COUNTING DETECTORS IN SPECTRAL COMPUTED TOMOGRAPHY IMAGING

(71) Applicants: Kabushiki Kaisha Toshiba, Minato-ku (JP); Toshiba Medical Systems Corporation, Otawara-shi (JP)

(72) Inventors: Xiaolan Wang, Buffalo Grove, IL (US); Yu Zou, Naperville, IL (US)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 289 days.

(21) Appl. No.: 13/770,638

(22) Filed: Feb. 19, 2013

(65) Prior Publication Data
US 2014/0233693 A1  Aug. 21, 2014

(51) Int. Cl.
*A61B 6/03* (2006.01)
*G01T 1/36* (2006.01)
(Continued)

(52) U.S. Cl.
CPC .............. *A61B 6/582* (2013.01); *A61B 6/4241* (2013.01); *A61B 6/5294* (2013.01); *G01T 1/365* (2013.01);
(Continued)

(58) Field of Classification Search
CPC ...... A61B 6/42; A61B 6/4208; A61B 6/4241; A61B 6/4266; A61B 6/48; A61B 6/482; A61B 6/488; A61B 6/52; A61B 6/5211; A61B 6/5294; A61B 6/58; A61B 6/582; A61B 6/583; A61B 6/032; G01N 23/06; G01N 23/08; G01N 23/083; G01N 23/087; G06T 1/18; G06T 1/20; G06T 1/24; G06T 1/29; G06T 1/2907; G06T 1/2992; G06T 1/36; G06T 1/365; G06T 1/366; G06T 1/00; G06T 1/007; G06T 11/003; G06T 11/006; G06T 11/008; G06T 19/20; G06T 2207/10072; G06T 2207/10081; G06T 2207/20; G06T 2211/00; G06T 2211/40; G06T 2211/408; G06T 2211/416; G06T 2211/421; G06T 2211/424; G06T 2211/436
USPC ........... 378/5, 8, 19, 20, 56, 62, 91, 95, 98.9, 378/162, 165, 204, 207, 210, 901
See application file for complete search history.

(56) References Cited

U.S. PATENT DOCUMENTS 6,246,747 B1  6/2001  Wear et al.
2003/0072409 A1 *  4/2003  Kaufhold et al. ............... 378/53
(Continued)

FOREIGN PATENT DOCUMENTS

JP  2004-174253  6/2004
JP  2009-513220  4/2009
(Continued)

OTHER PUBLICATIONS

International Search Report issued May 20, 2014, in Patent Application No. PCT/JP2014/053790 (with English translation of Category of cited Documents).

*Primary Examiner* — Anastasia Midkiff
(74) *Attorney, Agent, or Firm* — Oblon, McClelland, Maier & Neustadt, L.L.P.

(57) ABSTRACT

A method for photon count-loss calibration in a computed-tomography (CT) scanner, including capturing incident X-ray photons via a plurality of energy-discriminating detectors, determining photon counts of the captured incident X-ray photons in a plurality of energy windows at each energy-discriminating detector, and adjusting the determined photon counts in each energy window for each energy-discriminating detector based on a pre-determined photon count-loss look-up table and the determined photon counts.

10 Claims, 6 Drawing Sheets

(51) Int. Cl.
  G01N 23/087 (2006.01)
  A61B 6/00 (2006.01)
  G01T 1/17 (2006.01)
  G01T 1/29 (2006.01)

(52) U.S. Cl.
  CPC .. *A61B 6/032* (2013.01); *A61B 6/42* (2013.01); *A61B 6/4208* (2013.01); *A61B 6/4233* (2013.01); *A61B 6/482* (2013.01); *A61B 6/52* (2013.01); *A61B 6/58* (2013.01); *A61B 6/583* (2013.01); *G01N 23/087* (2013.01); *G01T 1/17* (2013.01); *G01T 1/2985* (2013.01); *G01T 1/36* (2013.01)

(56) References Cited

U.S. PATENT DOCUMENTS

| | | |
|---|---|---|
| 2004/0101104 A1 | 5/2004 | Avinash et al. |
| 2008/0260094 A1 | 10/2008 | Carmi |
| 2009/0129538 A1 | 5/2009 | Tkaczyk et al. |
| 2010/0027738 A1 | 2/2010 | Carmi |
| 2011/0155899 A1 | 6/2011 | Dror et al. |
| 2012/0085915 A1 | 4/2012 | Baeumer et al. |
| 2012/0087463 A1 | 4/2012 | Greenberg et al. |
| 2012/0128131 A1* | 5/2012 | Kraft et al. ............ 378/207 |
| 2014/0105370 A1 | 4/2014 | Yamakawa et al. |

FOREIGN PATENT DOCUMENTS

| | | |
|---|---|---|
| JP | 2010-511169 | 4/2010 |
| JP | 2012-187143 | 10/2012 |
| WO | WO 01/33252 A1 | 5/2001 |
| WO | WO 2007/049168 A2 | 5/2007 |
| WO | WO 2008/065564 A2 | 6/2008 |
| WO | WO 2011/090534 A2 | 7/2011 |
| WO | WO 2012/123845 A1 | 9/2012 |
| WO | WO 2012/144589 A1 | 10/2012 |

* cited by examiner

APPARATUS AND METHOD FOR COUNT LOSS CALIBRATION OF PHOTON-COUNTING DETECTORS IN SPECTRAL COMPUTED TOMOGRAPHY IMAGING

FIELD

Embodiments disclosed herein generally relate to computed tomography (CT). In particular, embodiments disclosed herein relate to an apparatus and method for count loss calibration of photon-counting detectors in spectral CT imaging.

BACKGROUND

X-ray tomographic imaging, in its simplest expression, is an X-ray beam traversing an object, and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-rays from the generator, the details of the geometry and characteristics of the detector, and the capacity of the acquisition system are all elements that affect how reconstruction is performed.

Figure 1:
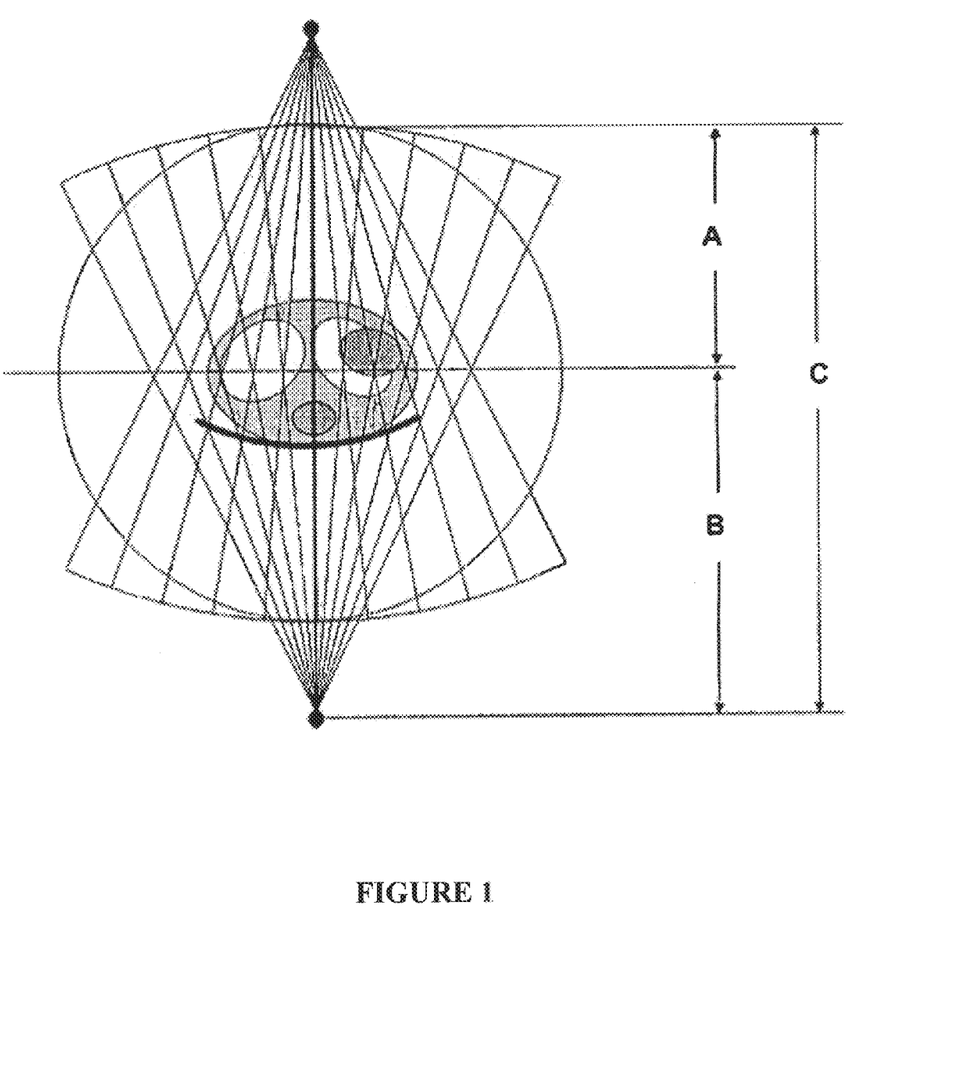
FIG. 1 illustrates an X-ray source emitting an X-ray beam forming a fan, traversing an object.

In one of many possible geometries, an X-ray source on top of the graph shown in FIG. 1 is emitting an X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Thus, the entire X-ray generator and detector assembly will rotate around the patient. Mathematical considerations show that the tomographic conditions are met when a scan of 180 degrees plus the fan angle is performed.

Conventional X-ray detectors integrate the total electrical current produced in a radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon counting and individual pulse-height analysis may be used. These X-ray detectors are made possible by the availability of fast semiconductor radiation sensor materials with room temperature operation and good energy resolution, combined with application-specific integrated circuits (ASICs) suitable for multi-pixel parallel readout and fast counting.

One major advantage of such photon-counting detectors is that, when combined with pulse-height analysis readout, spectral information can be obtained about the attenuation coefficient in the object. A conventional CT measures the attenuation at one average energy only, while in reality, the attenuation coefficient strongly depends on the photon energy. In contrast, with pulse-height analysis, a system is able to categorize the incident X-ray photons into several energy bins based on their detected energy. This spectral information can effectively improve material discrimination and target contrast, all of which can be traded for a dose reduction to a patient.

Using such photon-counting detectors for medical CT applications requires very high X-ray flux in most CT tasks. In a routine CT scan, as many as $10^8$ photons, or even more, can hit one detector element every second. Accordingly, photon-counting detectors suffer from count loss under high rate X-ray irradiation, e.g., in a clinical CT scan. Photon count loss may occur due to, e.g., detector crystal polarization or pulse pileup.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Embodiments disclosed herein relate to an apparatus and method for count loss calibration of photon-counting detectors in spectral CT imaging.

In one embodiment, there is provided a method for photon count-loss calibration in a computed-tomography (CT) scanner, comprising capturing incident X-ray photons via a plurality of energy-discriminating detectors, determining photon counts of the captured incident X-ray photons in a plurality of energy windows at each energy-discriminating detector, and adjusting the determined photon counts in each energy window for each energy-discriminating detector based on a pre-determined photon count-loss look-up table and the determined photon counts.

In one embodiment, there is provided a CT apparatus, comprising a CT scanner including an X-ray source, a detector including a plurality of energy-discriminating detectors capturing incident X-ray photons emitted from the X-ray source, and a processor configured to determine photon counts of the captured incident X-ray photons in a plurality of energy windows at each energy-discriminating detector, and adjust the determined photon counts in each energy window for each energy-discriminating detector based on a pre-determined photon count-loss look-up table and the determined photon counts.

In one embodiment, there is provided a method to determine a photon count-loss look-up table for calibrating photon counts detected at a plurality of energy-discriminating detectors in a computed-tomography (CT) apparatus, the method comprising: (1) emitting X-ray photons, under pre-determined scan parameters, from an X-ray source, to a phantom arranged within the CT apparatus, the phantom including a pre-determined basis material and having a pre-determined thickness; (2) capturing incident X-ray photons at the plurality of energy-discriminating detectors; (3) detecting the photon counts of the captured incident X-ray photons in a plurality of energy windows at each energy-discriminating detector; (4) determining true photon counts based on the pre-determined basis material, the pre-determined thickness, and the pre-determined scan parameters; and (5) storing, in the photon count-loss look-up table, the determined true photon counts and the detected photon counts in association with parameters representing the pre-determined basis material and the pre-determined thickness, and in association with the pre-determined scan parameters.

Figure 2:
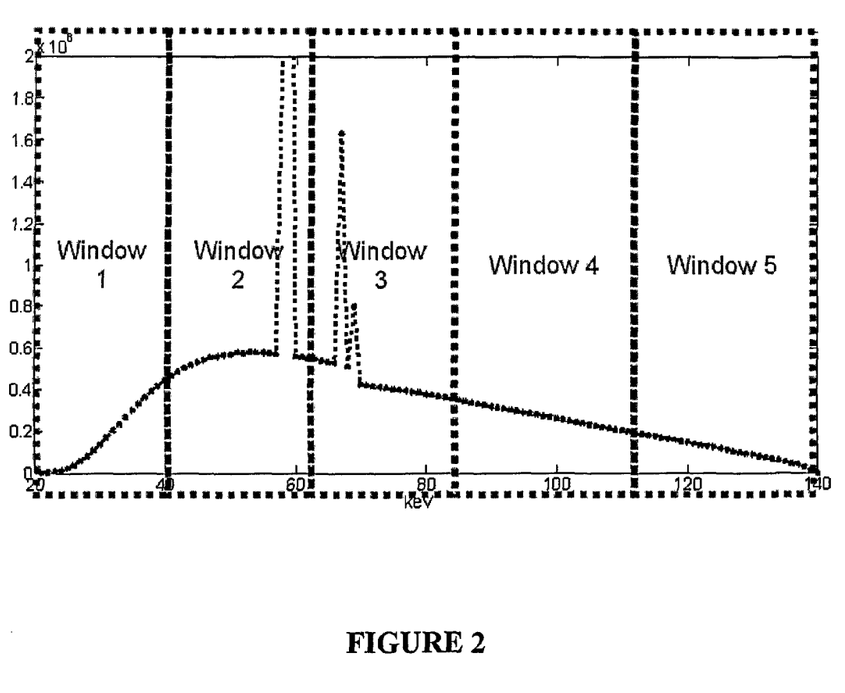
FIG. 2 illustrates an example response of a photon-counting detector in five energy windows.

In another embodiment, there is provided an apparatus to determine a photon count-loss look-up table for calibrating photon counts detected in a computed-tomography (CT) apparatus, the apparatus comprising: (1) an X-ray source configured to emit X-ray photons, under pre-determined scan parameters, from an X-ray source, to a phantom arranged within the CT apparatus, the phantom including a pre-determined basis material and having a pre-determined thickness; (2) a plurality of energy-discriminating detectors configured to capture incident X-ray photons and to detect the photon counts of the captured incident X-ray photons in a plurality of energy windows; (3) a processor configured to determine true photon counts based on the pre-determined basis material, the pre-determined thickness, and the pre-determined scan parameters; and (4) a memory configured to store, in the photon count-loss look-up table, the determined true photon counts and the detected photon counts in association with parameters representing the pre-determined basis material and the pre-determined thickness, and in association with the pre-determined scan parameters Turning now to the drawings, FIG. 2 shows an example response of a photon-counting detector in five pre-defined, non-overlapping energy windows. Photon counting detectors suffer from count loss under high rate X-ray irradiation, e.g., in a clinical CT scan. Photon count loss may occur due to, e.g., detector crystal polarization or pulse pileup. Accordingly, instead of counting all the incident photons accurately, the actual detected count is a function of incident count rate and X-ray spectra, as both polarization and pulse pileup are rate- and spectra-dependent. If left un-calibrated for, data inconsistency may occur between calibration scans and patient scans, resulting in degraded image quality and diminished diagnostic power.

According to one embodiment, a count loss calibration method is provided. Such a method may be used in addition to other calibration procedures available on existing CT scanners. The true-verses-detected response of a photon-counting detector is count-rate and spectra dependent. An X-ray spectrum is determined by protocol (kVp), filtration method, and patient attenuation. Basis material decomposition results may be used to parametrically describe patient attenuation. Count rate is determined by spectra and technique (mA). According to one embodiment, for count loss calibration, specially designed calibration phantoms (e.g., wedges consisting of different thicknesses of basis materials) are scanned under different protocols (kVp), techniques (mA), and filtration methods (e.g., bow-tie filters embedded in a CT scanner). Then, the true-verses-detected count relationship is calibrated and stored to be used for patient scans, where the count loss is corrected iteratively based on calibration results.

Figure 3:
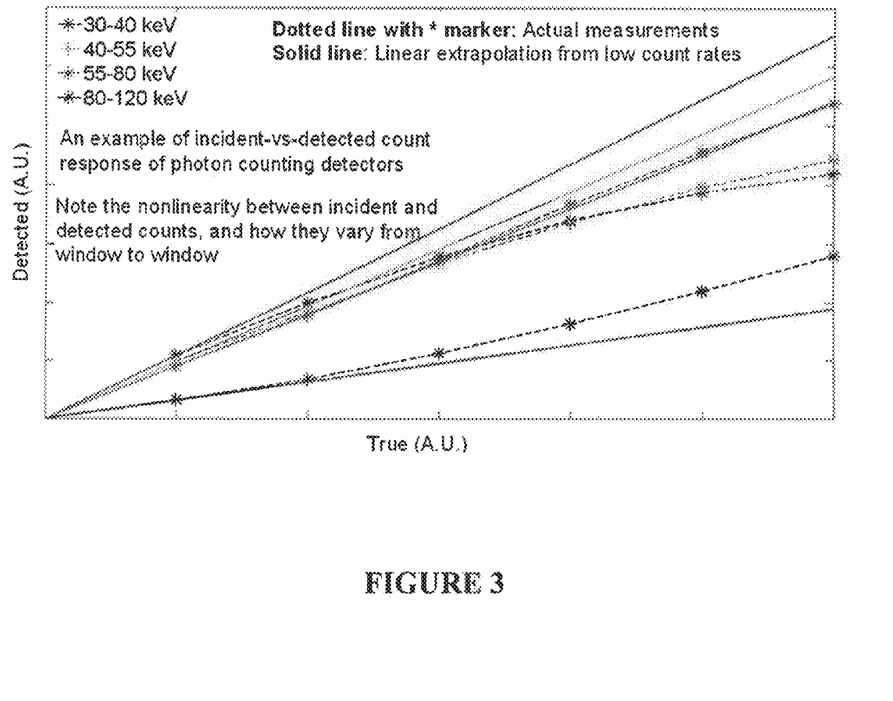
FIG. 3 illustrates an example of incident-verses-detected count response of a photon-counting detector with multiple energy windows.

FIG. 3 illustrates an example of incident-verses-detected count response of a photon counting detector. As shown in FIG. 3, there is non-linearity between incident and detected counts, and the relationship between incident and detected counts varies from window to window.

Figure 4:
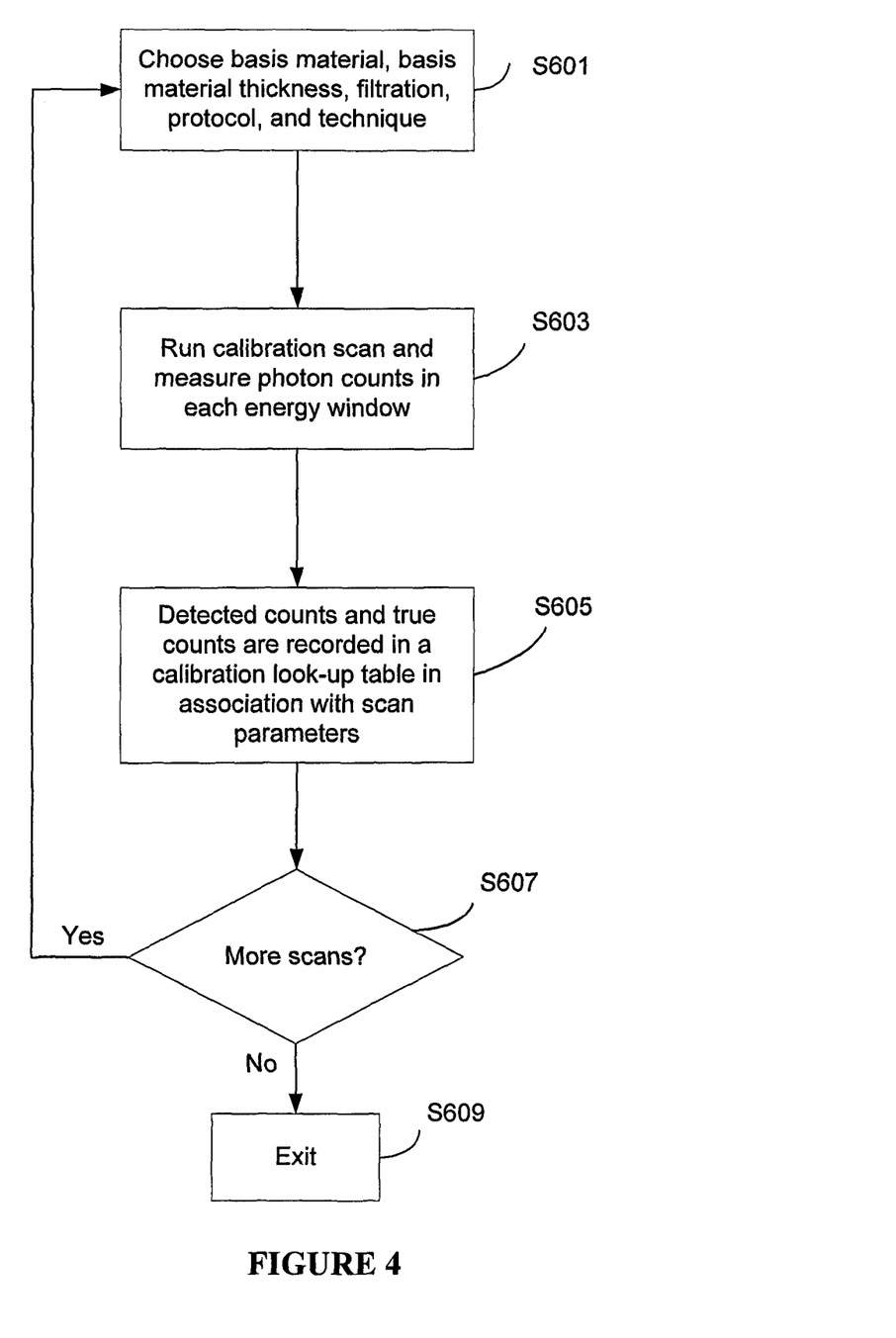
FIG. 4 illustrates a flowchart of a method of the present disclosure for determining a window-by-window look-up table for a count rate detector.

FIG. 4 illustrates a flowchart of a method of the present disclosure for determining a window-by-window look-up table for a count-rate detector for different spectra (described by $\{L_1, L_2\}$, kVp, and filtration method) and mA combinations.

In step S601, calibration scan parameters are chosen, i.e., basis material and thickness of basis material of phantom ($\{L_1, L_2\}$), protocol (kVp), technique (mA), and filtration method (e.g., bowtie). Based on this information, $\{I_{true,k}\}$ values are calculated. Recently developed methods to accurately compute $\{I_{true,k}\}$ based on these scan parameters have been developed. Various vendors have provided established and proven software for this purpose, but the software is often proprietary.

In step S603, a calibration scan is performed and the detected photon counts in each energy window, $\{I_{detected,k}\}$, are measured.

In step S605, the detected counts, $\{I_{detected,k}\}$ and true counts, $\{I_{true,k}\}$ are recorded in a calibration look-up table in association with the calibration scan parameters.

In step S607, the process checks if there are more calibration scans, and when there are more calibration scans, the process goes to step S601. Otherwise, the process exits at step S609.

Figure 5:
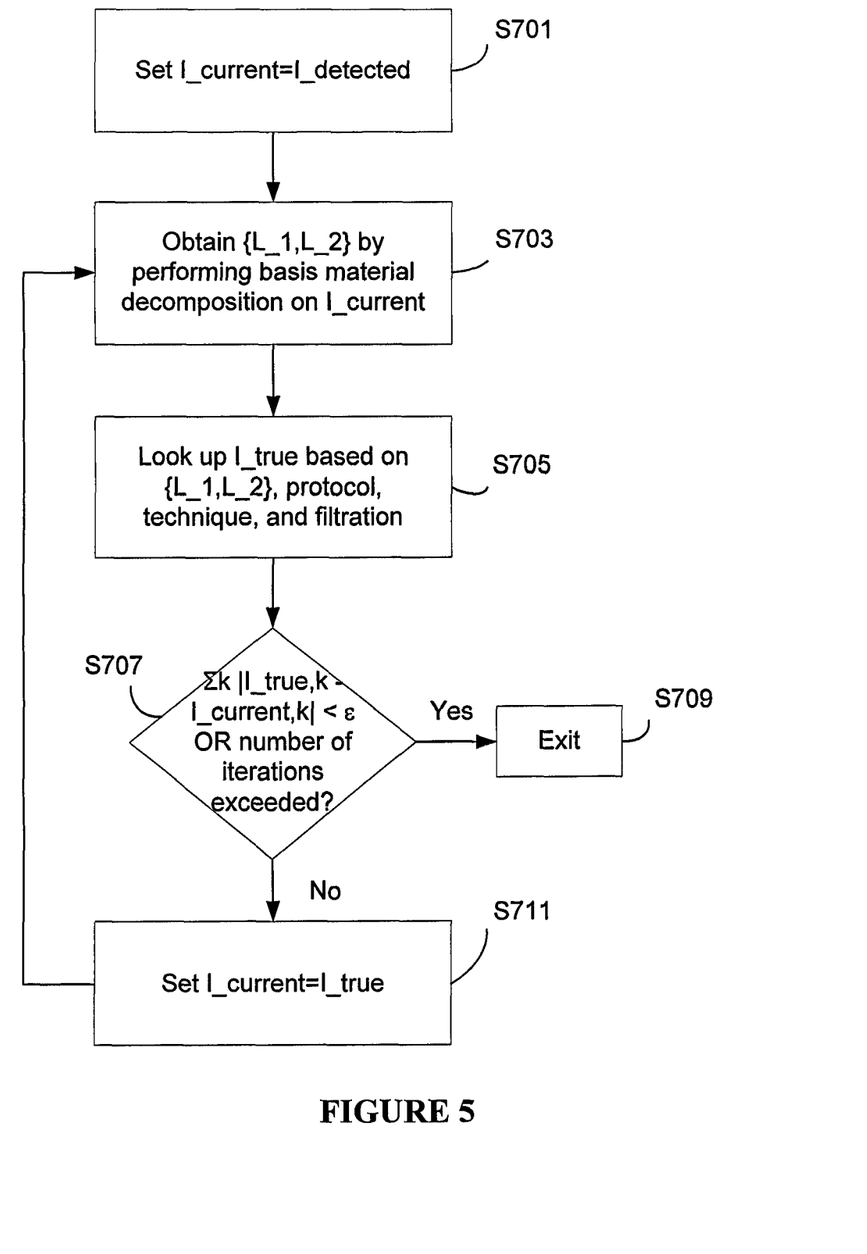
FIG. 5 illustrates a flowchart of a method of the present disclosure for compensating for photon count loss during patient scans.

FIG. 5 illustrates a flowchart of a method of the present disclosure for compensating for photon count-loss during patient scans. During a patient scan, based on the detected counts and a calibration look-up table, count loss is iteratively compensated for. This is done for each energy window of each photon-counting detector in the system. The method of FIG. 5 is performed for each detector independently.

In FIG. 5, steps S701, S705, S707, and S711 are performed for each of the energy windows before moving to the next step.

In step S701, iteration parameter $\{I_{current,k}\}$ is initialized to be equal to the detected count $\{I_{detected,k}\}$ for each energy window k.

In step S703, basis material decomposition is performed based on $\{I_{current,k}\}$ from all energy windows to obtain $\{L_1, L_2\}$. In one embodiment, basis material decomposition uses X-ray measurements at multiple energies to calculate the basis material thickness/density, which quantitatively describes an object's X-ray attenuation property and its energy dependence. Such decomposition is only feasible with more than one energy, and thus is uniquely used in spectral CT imaging. $\{L_1, L_2\}$ can be mathematically calculated given $\{I_{current,k}\}$ (k=1, . . . , # of total energy windows). The exact implementation is often vendor-specific and proprietary and requires exact knowledge of the type of basis materials and the X-ray spectra incident on the object.

In step S705, given $\{I_{detected,k}\}$, $\{L_1, L_2\}$ and scan parameters, e.g., protocol, filtration method, and technique, the calibration look-up table is used to obtain $\{I_{true,k}\}$ for each energy window k.

In step S707, the process checks if the iteration has converged by checking if a pre-determined number of iterations has been performed, and checking if the following condition is satisfied:

$$\Sigma k |I_{true,k} - I_{current,k}| < \epsilon,$$

where $\epsilon$ is a tolerance parameter determined by the eventual image quality, which is application- and target-specific. For example, if a low-contrast target is imaged, lower error can be tolerated. When the iteration has converged, i.e., if a predetermined number of iterations have been performed or the above condition is satisfied, the process exits in step S709. Otherwise, the process proceeds to step S711.

In step S711, iteration parameter $I_{current}$ is set equal to $I_{true}$ and the process goes to step S703 for the next iteration.

After completion of the process of FIG. 5, data pre-processing and image reconstruction may be performed using $I_{true}$.

The process of FIG. 5 is repeated if an energy-window setting is changed, e.g., if the position and width of some or all energy windows change, which is required when application and scan conditions change.

The disclosed embodiments compensate for rate- and spectra-dependent detector count loss.

The disclosed embodiments obtain accurate spectral measurements that are independent of incident count rate and spectra.

Figure 6:
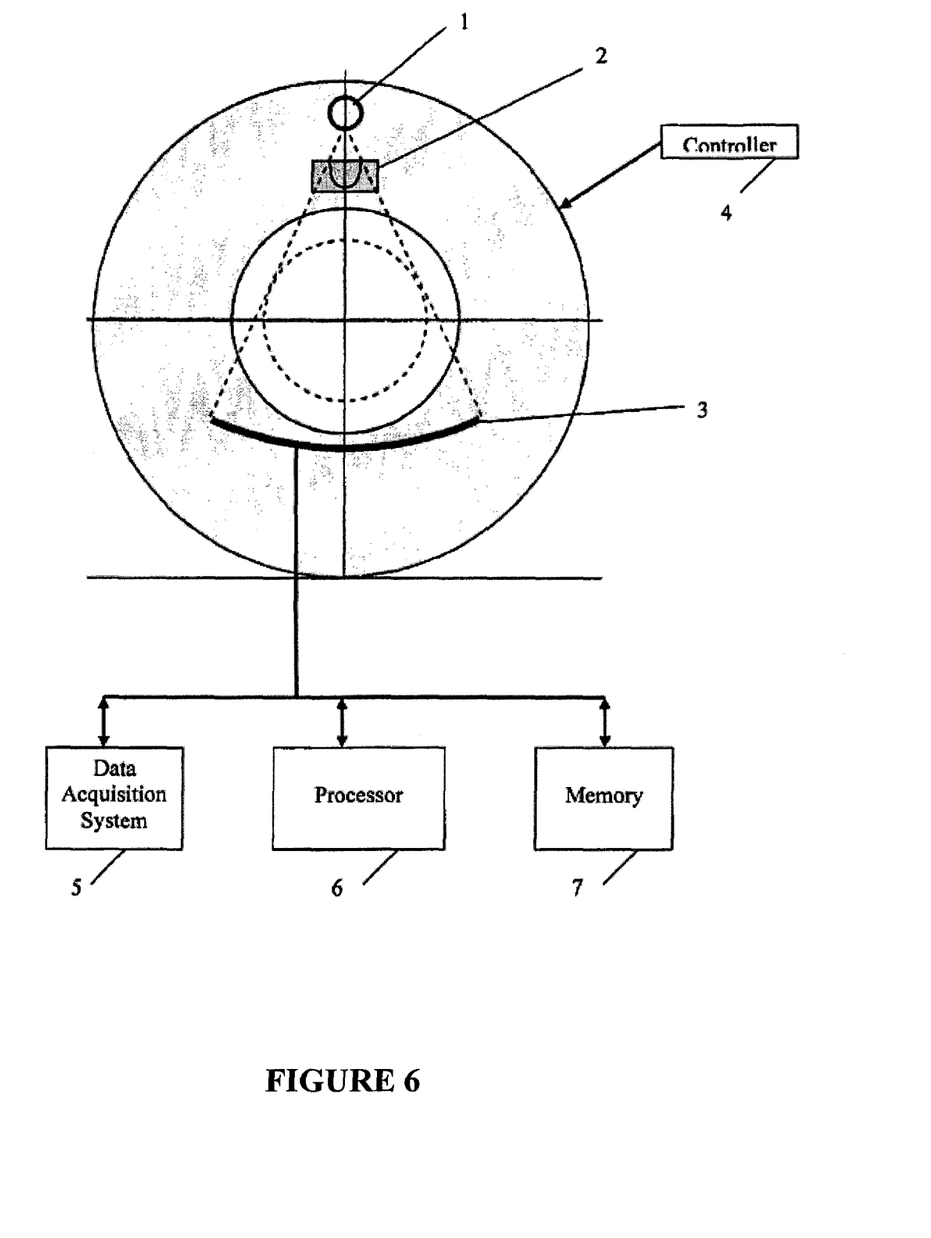
FIG. 6 is a diagram of a mechanically simplified CT apparatus.

FIG. 6 illustrates the basic structure of a CT apparatus that can include the photon-counting detectors described herein. The CT apparatus of FIG. 6 includes an X-ray tube 1, filters and collimators 2, and detector 3. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection data acquired by the data acquisition system. In one embodiment, the reconstruction processor makes use of a "map" of the detector that indicates which detector elements are collimated (e.g., tunnels) and which are not. The processor and data acquisition system make use of a memory 7, which is configured to store e.g., data obtained from the detector, the map of the detector, and reconstructed images.

In one embodiment, the processor is programmed to determine photon counts of the captured incident X-ray photons in a plurality of energy windows at each energy-discriminating detector, and to adjust the determined photon counts in each energy window for each energy-discriminating detector based on a pre-determined photon count-loss look-up table and the determined photon counts.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

The disclosed embodiments effectively incorporate the angular dependency of detector detection efficiency into current CT data acquisition models.

The disclosed embodiments compensate for data inconsistency due to the angular dependency of detector response as well as any possible residual effect from count rate dependency and energy resolution blurring.

As would be clear to one of ordinary skill in the art, the above-disclosed methods for photon count-loss calibration apply to all CT scanner geometries, including single-slice and multi-slice scanners. Moreover, the disclosed methods can be used with all CT beam types, including parallel beams, fan-beams, and cone-beams.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for photon count-loss calibration in a computed-tomography (CT) scanner, comprising:
   capturing incident X-ray photons via a plurality of energy-discriminating detectors;
   determining photon counts of the captured incident X-ray photons in a plurality of energy windows at each energy-discriminating detector; and
   adjusting the determined photon counts in each energy window for each energy-discriminating detector based on a pre-determined photon count-loss look-up table and a basis material decomposition obtained from the determined photon counts.

2. The method of claim 1, wherein the adjusting step comprises:
   defining, for a specific energy window of a specific energy-discriminating detector, a first photon count to be equal to a photon count among the determined photon counts corresponding to the specific energy window of the specific energy-discriminating detector;
   obtaining the basis material decomposition based on the first photon count;
   determining an estimated true photon count based on the pre-determined photon count-loss look-up table and the obtained basis material decomposition, the specific energy window, and a plurality of scan parameters;
   calculating a difference between the estimated true photon count and the first photon count; and
   changing the first photon count to be equal to the estimated true photon count and repeating the obtaining, determining, calculating, and changing steps when an absolute value of the calculated difference is greater than a pre-determined threshold.

3. A computed-tomography (CT) apparatus, comprising:
a CT scanner including an X-ray source;
a detector including a plurality of energy-discriminating detectors capturing incident X-ray photons emitted from the X-ray source; and
a processor configured to
    determine photon counts of the captured incident X-ray photons in a plurality of energy windows at each energy-discriminating detector, and
    adjust the determined photon counts in each energy window for each energy-discriminating detector based on a pre-determined photon count-loss look-up table and a basis material decomposition obtained from the determined photon counts.

4. The CT apparatus of claim 3, wherein, in adjusting the determined photon count, the processor is further configured to:
define, for a specific energy window of a specific energy-discriminating detector, a first photon count to be equal to a photon count among the determined photon counts corresponding to the specific energy window of the specific energy-discriminating detector;
obtain the basis material decomposition based on the current first photon count;
determine an estimated true photon count based on the pre-determined photon count-loss look-up table and the obtained basis material decomposition, the specific energy window, and a plurality of scan parameters;
calculate a difference between the estimated true photon count and the first photon count; and
change the first photon count to be equal to the estimated true photon count, and repeat the obtaining, determining, calculating, and changing steps when an absolute value of the calculated difference is greater than a pre-determined threshold.

5. A method to determine a photon count-loss look-up table for calibrating photon counts detected at a plurality of energy-discriminating detectors in a computed-tomography (CT) apparatus, the method comprising:
emitting X-ray photons, under pre-determined scan parameters, from an X-ray source, to a phantom arranged within the CT apparatus, the phantom including a pre-determined basis material and having a pre-determined thickness;
capturing incident X-ray photons at the plurality of energy-discriminating detectors;
detecting the photon counts of the captured incident X-ray photons in a plurality of energy windows at each energy-discriminating detector;
determining estimated true photon counts based on the pre-determined basis material, the pre-determined thickness, and the pre-determined scan parameters; and
storing, in the photon count-loss look-up table, the determined estimated true photon counts and the detected photon counts in association with parameters representing the pre-determined basis material and the pre-determined thickness, and in association with the pre-determined scan parameters.

6. An apparatus to determine a photon count-loss look-up table for calibrating photon counts detected in a computed-tomography (CT) apparatus, the apparatus comprising:
an X-ray source configured to emit X-ray photons, under pre-determined scan parameters, from an X-ray source, to a phantom arranged within the CT apparatus, the phantom including a pre-determined basis material and having a pre-determined thickness;
a plurality of energy-discriminating detectors configured to capture incident X-ray photons and to detect the photon counts of the captured incident X-ray photons in a plurality of energy windows;
a processor configured to determine estimated true photon counts based on the pre-determined basis material, the pre-determined thickness, and the pre-determined scan parameters; and
a memory configured to store, in the photon count-loss look-up table, the determined estimated true photon counts and the detected photon counts in association with parameters representing the pre-determined basis material and the pre-determined thickness, and in association with the pre-determined scan parameters.

7. The method of claim 1, wherein the pre-determined photon count-loss look-up table includes estimated true photon counts corresponding to the obtained basis material decomposition, the specific energy window, and a plurality of scan parameters.

8. The method of claim 1, wherein the adjusting step comprises:
calculating a difference between an estimated true photon count and a first photon count; and
changing the first photon count, and repeating the calculating and changing steps when the calculated difference is greater than a pre-determined threshold.

9. The CT apparatus of claim 3, wherein the pre-determined photon count-loss look-up table includes estimated true photon counts corresponding to the obtained basis material decomposition, the specific energy window, and a plurality of scan parameters.

10. The CT apparatus of claim 3, wherein, in adjusting the determined photon count, the process is further configured to:
calculate a difference between an estimated true photon count and a first photon count; and
change the first photon count, and repeat the calculating and changing steps when the calculated difference is greater than a pre-determined threshold.

* * * * *